United States Patent [19]

Evans

[11] Patent Number: 4,973,770

[45] Date of Patent: Nov. 27, 1990

[54] MANUFACTURE OF ORGANIC NITRO COMPOUNDS

[75] Inventor: Colin M. Evans, Willowdale, Canada

[73] Assignee: C-I-L, Inc., Ontario, Canada

[21] Appl. No.: 284,700

[22] Filed: Dec. 15, 1988

[51] Int. Cl.$^5$ .................. C07C 205/06; C07C 205/07; C07C 205/05

[52] U.S. Cl. .................................... 568/929; 568/928; 568/937; 568/927

[58] Field of Search ................ 260/688; 568/927, 928, 568/929, 937

[56] References Cited

U.S. PATENT DOCUMENTS

| | | | |
|---|---|---|---|
| 2,256,999 | 9/1941 | Castner | 260/645 |
| 2,512,587 | 6/1950 | Stengel | 260/688 |
| 2,654,788 | 10/1953 | Marshall, Jr. | |
| 2,737,522 | 11/1956 | Nilsson | 260/467 |
| 2,951,866 | 9/1960 | McKinney, Jr. | 260/467 |
| 3,053,908 | 9/1962 | Kouba et al. | |
| 3,111,538 | 11/1963 | Stow, Jr. | 260/467 |
| 3,115,527 | 12/1963 | Drimus et al. | |
| 3,160,669 | 12/1964 | Terao et al. | 260/645 |
| 3,378,596 | 4/1968 | Toops, Jr. et al. | |
| 3,431,312 | 3/1969 | Toischer et al. | 260/645 |
| 4,021,498 | 5/1977 | Alexandersen et al. | 260/645 |
| 4,091,042 | 5/1978 | Alexandersen et al. | 260/645 |
| 4,251,455 | 2/1981 | Gebauer | 260/467 |

OTHER PUBLICATIONS

Chemical Engineering Handbook, 6th Edition, pp. 21-57, 21-58 (Perry).

*Primary Examiner*—John S. Maples
*Assistant Examiner*—Valerie Fee
*Attorney, Agent, or Firm*—Cushman, Darby & Cushman

[57] ABSTRACT

Process for the mononitration of a nitratable organic compound, such as benzene, with a mixed acid in which one of the reactants is delivered into a body of the other reactant in the form of ultra-fine droplets through an atomizing nozzle or similar orifice. The process is economic to construct and operate, is safe and simple to control and leads to a low cost, substantially pure product.

4 Claims, 2 Drawing Sheets

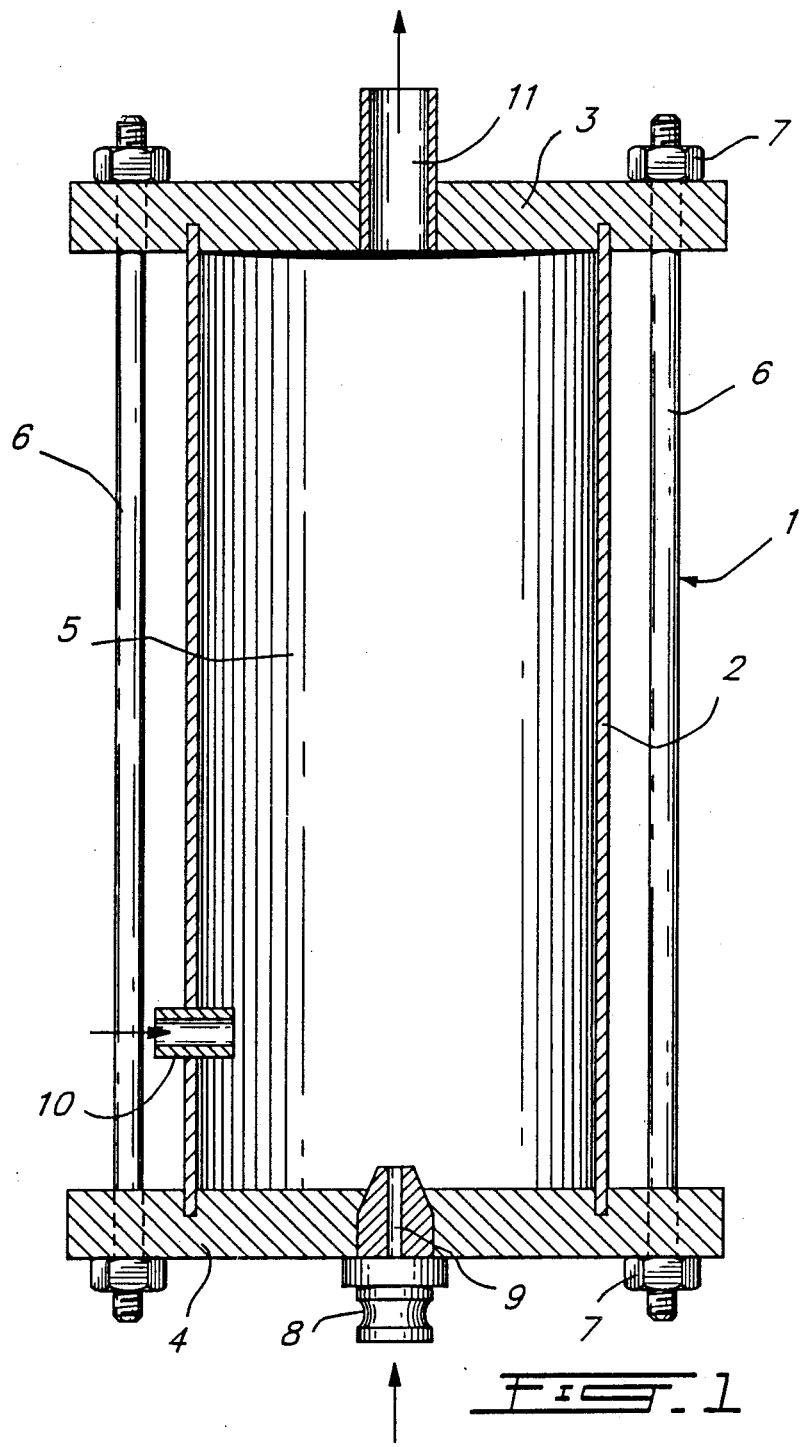

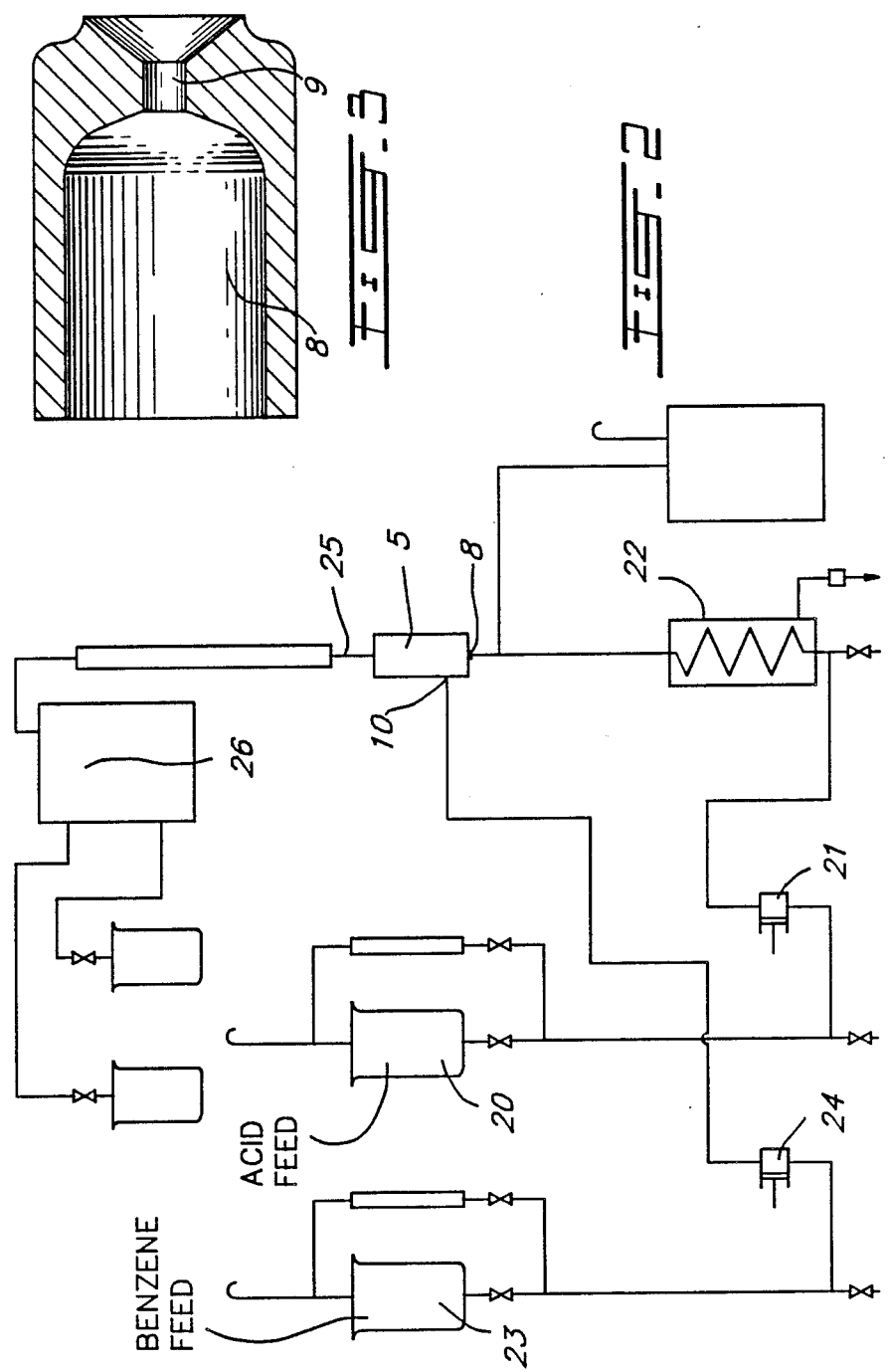

4,973,770

MANUFACTURE OF ORGANIC NITRO COMPOUNDS

TECHNICAL FIELD

The present invention relates to a continuous process for the production of mononitrobenzene. In particular, the invention relates to an improved, continuous adiabatic process for the production of nitrobenzene.

BACKGROUND OF THE INVENTION

The process of nitrating benzene is old and well known and has been commerically practiced for many years to yield mononitrobenzene used, in turn, in the production of aniline. Conventionally, the manufacture of nitrobenzene comprises the batchwise, stepwise or continuous addition of mixed nitric acid and sulphuric acid to benzene. This nitration reaction may be conducted at temperatures controlled in the range of 60°-70° C. with the removal of the heat of reaction or it may be conducted under adiabatic conditions described by Castner in U.S. Pat. No. 2,256,999, where little or no heat of reaction is removed and in which the heat of reaction is utilized in later stages of spent acid reconcentration. The mixed nitric/sulphuric acid employed by Castner in his adiabatic process comprises a mixture of 75% strength sulphuric acid together with sufficient 63% strength nitric acid such that the mixture has a content of 3% nitric acid. In an improved adiabatic process described by Alexanderson et al in U.S. Pat. No. 4,091,042, wherein the reaction is carried out under superatmospheric pressure, the mixed acid contains 3-8.5% nitric acid, from 58.5-70.0% sulphuric acid and not less than about 25% of water. In both the Castner and Alexanderson et al processes, the mixed acid and a stoichiometric excess of benzene are admixed and reacted together under vigorous agitation at temperatures of 100° C. or greater.

Since the acid phase and the benzene phase are not miscible, the reaction rate and the reaction efficiency between the phases are largely limited by mass transfer; that is, by the ability to expose large interfacial areas of each of the phases to each other. As the interfacial areas are increased, the reaction rate between the phases is enhanced. In conventional nitrobenzene production facilities, these interfacial areas are normally created by reacting the two phases in one or more agitated vessels where high shear forces are applied to the liquids. Alexanderson et al described the use of "vigorous agitation" to disperse the benzene throughout the reaction mixture. In other similar nitration processes, various means have been proposed to bring together the immiscible phases. In the process of Toischer et al (U.S. Pat. No. 3,431,312), a cascade of stirred reaction chambers is used in the nitration of toluene. In the process of Terao et al (U.S. Pat. No. 3,160,669), a compartmentalized, elongated, baffled reaction zone containing a series of agitating blades fixed to a stirrer shaft are provided. In the process of Nilsson (U.S Pat. No. 2,737,522), glycerine is nitrated with mixed acid by injecting a pressurized jet of acid into a venturi-shaped reaction zone to contact a similar jet of glycerine within the zone where intimate mixing is caused to take place. McKinney in U.S. Pat. No. 2,951,866 describes the use of a tubular reaction zone wherein separate streams of polyhydric alcohol and nitrating acid are impinged upon each other to form a turbulent reaction mixture. A similar tubular reactor is described by Stow in U.S. Pat. No. 3,111,538. Gebauer, in U.S. Pat. No. 4,251,455, makes reference to the process of German Patent No. 1,135,876 wherein the nitration of polyhydric alcohols is achieved by impinging the two reactants upon each other. In the Chemical Engineering Handbook (Perry), 6th Edition, a number of methods are proposed to achieve intimate mixing or contact between liquids including, for example, in-line motionless mixers, mechanical agitation, gas agitation, jet mixers, injectors, orifice mixers and nozzle mixers.

None of the aforesaid methods for achieving large interfacial areas of contact between immiscible liquid phases is completely satisfactory nor has any method, other than mechanical agitation, been used commerically to any degree in the manufacture of mononitrobenzene. These methods either suffer from high capital and maintenance costs and high power requirements, as in the case of agitated vessels, or they are difficult to control in terms of optimum reaction efficiency as in the case of impinging streams or jets. There, therefore, remains a need for a benzene nitration process which is economic to construct and operate, which is safe and simple to control and which leads to optimum output of reaction product at least possible cost.

DISCLOSURE OF THE INVENTION

It is an object of this invention to provide a process for the reliable manufacture of mononitrobenzene which obviates or mitigates the known deficiencies of the prior art processes.

It is a further object of this invention to provide a process for the safe and energy-efficient manufacture of mononitrobenzene on a continuous basis.

Therefore, according to this invention there is provided a process for the continuous production of mononitrobenzene or other organic nitro compound which process comprises simultaneously and continuously introducing into a reaction chamber separate liquid streams of a mixed nitrating acid component and an immiscible organic component, one of the said components, for example, the mixed acid component being introduced into the said organic component through turbulence inducing means which constricts the flow of said acid component such as to cause its disruption to form fine droplets of a desired size upon its emergence into the reaction chamber, said turbulence inducing means further causing said mixed acid to emerge in a flow pattern and at a flow rate sufficient to cause the droplets so formed to come into contact with a sufficient quantity of the organic component to provide for reaction between the said acid and the said organic component to form an organic nitro compound. Alternatively, the organic component may be introduced through the turbulence-inducing means into the mixed acid component within the reaction chamber to form the organic nitro compound.

The means for causing disruption of one or the other of the reactants may be any form of pressure atomiser i.e. a device wherein the liquid is forced under pressure through an orifice to discharge in the form of droplets of a size acceptable for the purpose defined herein.

Thus, it will be appreciated that this process has the advantage that the desired organic nitro compound product can, in most instances, be produced in only one step without reliance on liquid/liquid shear and so the use of the expensive and energy inefficient shear mixing devices typically required is avoided. In the event that less than complete conversion of the organic component is achieved in a single reaction chamber, a second chamber may be employed wherein the product of the first chamber is subjected to further reaction by exposure to additional amounts of one or the other component in droplet form. Alternatively, a single reaction chamber may be coupled with, for example, an in-line mixer or orifice plate wherein a final or "polishing" nitration is accomplished through intermixing of the phases..

Preferably, the flow of the organic component, for example, benzene is constricted and atomized by means of an orifice in said turbulence-inducing means wherein the path length ($L_n$) through said orifice is sufficient so as to provide for the greatest pressure gradient with minimum losses in energy. The diameter of the orifice $D_o$ (m) should be selected in accordance with the intended volume flow rate Q (m$^3$.s$^{-1}$) and the desired droplet size. It can be shown that maximum possible droplet size $$D_{max} \alpha \frac{D_o^{3/2}}{Q^{\frac{1}{2}}}$$

(assuming that no mechanism for coalescence exists) so that for constant drop size, if flow rate is increased, e.g. 7-fold, the nozzle diameter should be increased approximately 2-fold. Suitable orifice sizes for the purposes set out herein may be in the range of about 0.001 m to about 0.02 m, preferably from 0.005 m to about 0.015 m.

Preferably, the means for causing disruption of the organic (benzene) component is a nozzle which discharges into the reaction chamber, advantageously in a readily replaceable manner for the purposes of nozzle exchange which nozzle is adapted to constrict flow sufficiently to cause turbulence in the stream of the benzene phase to provide for discharge of dispersed single droplets of a size comparable to the eddies in the flow created within the nozzle in use under operating conditions. The advantage of this arrangement is that it provides for localized break up of the benzene component directly into the mixed acid component which provides for localized energy dissipation and very efficient energy transfer. Thus, preferred arrangements provide for local energy dissipation rate ($\epsilon$) in the range of from $10^4$ to $10^8$ W/kg with most preferred rates being in excess of $10^6$ W/kg. Energy dissipation rate is routinely calculated (assuming Newtonian liquid behaviour) from knowledge of the path length $L_n$ (m) through the orifice of the nozzle, the pressure drop $VP_n$ (N.m$^{-2}$) across the nozzle, the density $\rho_F$ (kg.m$^{-3}$) of the mixed acid phase and the mean fluid velocity $\overline{U}$ (m.s.$^{-1}$) all of which can be readily measured. The pressure drop across the nozzle for a sharp edged orifice is shown by the following equation:

$$P_n = \tfrac{1}{2} \rho_F U^2 \quad (1)$$

and since $\frac{d}{dt}(E) = P = \frac{\text{work done}}{\text{unit time}} = FU$ and $$\epsilon = \frac{P}{m} \text{ i.e. } (W/kg)$$

then the specific power dissipation $\epsilon$ may be written as $$\epsilon = \frac{VP_n}{\rho_F} U \quad (2)$$

where $VP_n = \frac{\Delta P_n}{L_n}$ and from (1)

we have $\epsilon = \tfrac{1}{2} U^3 / L_n$

By virtue of this invention, selected droplet sizes are obtainable such that the average droplet size lies in a narrow range so that high populations of droplets of less than 8 μm, preferably about 4 μm or less, down to about 0.5 μm are consistently achievable. Ordinarily, it will be found that for a given set of process conditions, droplet sizes will lie within a relatively narrow range (save for a small proportion of droplets which arise from coalescence of formed droplets). Thus, for example, taking a flow rate of say 20 1.m$^{-1}$ for the benzene stream through a 4.6 mm diameter orifice, $D_{max} = 13$ μm where $$D_{max} \approx \left( \frac{8\gamma}{C_D \rho_C} \right)^{3/5} \epsilon^{-2/5}$$

whilst
$D_{average} = 3$ μm, where
$D_{average}$
where
$\gamma$ = interfacial tension (N.m$^{-1}$)
$C_D$ = drag coefficient of droplet
$\rho_C$ = density of the benzene phase (kg.m$^{-3}$)
$\epsilon$ = specific energy dissipation rate (W.kg$^{-1}$)
$U$ = dynamic benzene phase velocity (mhu.s$^{-1}$)

Thus the droplet size, and hence the exposed interfacial area, is controllable by flow rate and orifice dimensions. Flow of the benzene component is isotropic, turbulent flow. The velocities of flow and, hence, bulk Reynolds numbers (Re) associated with these conditions are in the range of from 30,000 to 500,000, depending on plant throughput, and, preferably, upwards of 50,000. The rate of flow of each stream is, preferably, controlled to provide for ratios of mixed acid component to benzene component by which a slight excess (1–10%) of benzene over the nitric acid content of the mixed acid is achieved.

More preferably, the nozzle is one capable of discharging a turbulent stream as a transient divergent sheet producing a divergent pattern ("solid cone") of droplets and may or may not impart a rotational motion element to said droplets. Such flow patterns may be obtained by use of nozzles known from the spray-drying art.

The nozzle, preferably, includes internal baffles or other means defining one or more tangential or helical passages to provide for a radial (helical) emergent flow superimposed on a linear divergent flow to produce a resultant helical flow which serves to enhance dispersion of the droplets rapidly formed on discharge. The advantage of this arrangement is that the helical flow creates a pressure gradient along the notional jet boundary which facilitates entrainment of the mixed acid component and mixing of droplets with the continuously formed mononitrobenzene reaction product.

The nozzle, preferably, has an exit cone angle of 70° or less. At 0° or very low exit nozzle cone angles, there is a pronounced tendency to produce a collimated narrow stream of the benzene component at higher stream velocities which is unsatisfactory for efficient reaction rates.

Operating pressures (back pressure in nozzle) are suitably in the range of from 10 psi to 200 psi, preferably, 30 psi to 135 psi and upwards, bearing in mind that the higher the pressure used the greater the energy available for droplet creation, the more efficient the chemical reaction becomes. It is likely that pressure exceeding 160 psi would be unnecessary for normal purposes.

The linear fluid velocity through the nozzle is typically from 5 to 40 ms$^{-1}$ and average droplet sizes of from 7 to 10 down to 1 or less $\mu$m are achieved.

As mentioned above, preferred nozzles are characterized by short and narrow constrictions so that the stream of the atomized phase passes rapidly through the nozzle constriction under a high pressure gradient. Nozzles which will be suitable for the purposes of this invention are commerically available (Spraying Systems Co., Wheaton, Illinois, U.S.A.).

Preferably, the dimensions of the reaction chamber are such as to minimize impingement of droplets on the walls of the chamber so as to mitigate the problem of coalescence of the droplets prior to complete chemical reaction. In other words, the zone of droplet formation and initial dispersion should desirably be remote from boundary surfaces. Conveniently, the reaction chamber is a cylindrical vessel having removable end closures, one of which has means providing for removal of continuously formed reaction product and waste acid. The removal of product is desirably continuous but it is possible to provide for continual removal of batches of product at selected intervals depending upon the capacity of the reaction chamber and rate of production of the organic nitro compound.

Preferably, also the mixed acid component is fed through a pipe passing directly into the reaction chamber in the region of the organic (benzene) droplet discharge from the nozzle and which is located adjacent to, but spaced sufficiently from the nozzle to minimize coalescence of droplets whilst enabling entrainment of the mixed acid stream in said droplet discharge. A suitable arrangement is to provide the nozzle centrally in an end wall of a cylindrical vessel defining the reaction chamber and to have the pipe for discharge of the mixed acid component passing through the cylindrical wall to emerge at a position close to the nozzle allowing said mixed acid stream to contact the benzene droplets discharged by said nozzle and pass into the continuously formed reaction product.

The point or points of discharge of the mixed acid component into the reaction chamber are capable of substantial adjustment both laterally (i.e. at right angles to the length dimension of the chamber), although probably there will be a longitudinal position beyond which insufficient entrainment (back mixing) of mixed acid will occur and efficient chemical reaction will be defeated.

The invention in one preferred aspect provides a process for producing mononitrobenzene comprising forming a turbulent jet of benzene, preferably having a Reynolds number of greater than about 50,000, subject to plant throughput, to produce droplets of a selected size within the range of from about less than 1 um to 10 um diameter and contacting said jet continuously in the region of droplet formation with mixed acid in an amount which is sufficient to provide essentially complete conversion of nitric acid and produce a mononitrobenzene containing substantially no di- nitrobenzene.

Most preferably, the predominant droplet size is from less than 1 μm to 2 μm. "Size" means the number average droplet diameter.

Employing prior art reaction apparatus wherein one component is injected into a second component, use is made of a velocity gradient between the components which provides a shearing force which creates a series of small droplets. Such shearing action is generally incapable of producing very fine droplets except under extreme condition. In the process of the present invention, no reliance is made on a velocity gradient between the phases and consequent liquid/liquid shear. Instead, fine droplets are produced from the organic material which droplets are thereafter distributed throughout the mixed acid. The degree of atomization and, consequently, the droplet size of the organic component can be adjusted by selecting the appropriate atomizing nozzle. The particle or droplet size distribution of the acid component is narrow.

Although not specifically tested, it is envisioned that the process of the present invention will also include the step of introducing both the mixed acid and the nitratable organic compound into the reaction chamber in the form of atomized jets.

DESCRIPTION OF THE DRAWINGS

The invention will now be further described by way of the following Examples and with reference to the accompanying drawings in which:

FIG. 1 is a cross-sectional view of an embodiment of a suitable reaction chamber apparatus used in the process of the invention;

FIG. 2 is a flow diagram of a typical adiabatic mononitrobenzene continuous preparation process employing one method of the invention; and FIG. 3 is a section through a nozzle suitable for the purpose of this invention.

DESCRIPTION OF THE BEST MODE

The invention is depicted in FIGS. 1 and 2 in terms of the introduction of a reaction stream of mixed nitrating acid containing from about 3-8.5% nitric acid, from 58.5-70.0% sulphuric acid and not less than about 25% of water into a stream of benzene or benzene-rich mononitrobenzene in the form of a turbulent jet of discrete acid droplets within the size range of about 1 to 10 um within a reaction chamber. It will be understood that the process of the invention may be reversed, that is, a turbulent jet of benzene may be delivered into a stream or body of mixed acid as described in the Example hereinbelow. It will also be understood that the process will be applicable to other nitrations or other chemical reactions which are mass transfer limited.

In FIG. 1, a reaction chamber apparatus, generally designated 1 is shown which consists of a cylindrical tube 2, upper end closure 3 and lower end closure 4. When assembled as shown, tube 2 and closures 3 and 4 define a chamber 5. The assembly can be held together, for example, by bolts 6 secured by threaded nuts 7. Centrally located in lower end closure 4 is an atomizing nozzle 8 having a narrow passage 9 therein. Mounted in the side wall of chamber 5 and passing through tube 2 is an inlet tube 10. This inlet tube is adjustable both laterally (i.e. at right angles to the longitudinal axis of the tube 2) and longitudinally (i.e. along the length of the tube 2). Located in upper end closure 3 is an exit or outlet port 11.

Reaction chamber apparatus 1 is adapted to receive a turbulent spray of droplets of a mixed nitrating acid component into a body of benzene with sufficient velocity to effect contact at a micron particle size level. The benzene component is continuously introduced into chamber 5 through inlet tube 10 where it is entrained by a high velocity atomized stream or spray of the acid component introduced continuously into chamber 5 through passage 9 in nozzle 8. The intermixing of the two phases permits rapid chemical reaction between particles of a size as small as 2 microns or less.

To achieve optimum reaction conditions between the two components, several variable factors may be adjusted by trial and error to produce the desired end product. The diameter of chamber 5, the velocity of the atomized stream passing into chamber 5 through nozzle passage 9, the type or angle of spray achieved by nozzle 8, and the location of inlet tube 10 may all be manipulated to produce a desired end product in the most effective manner.

The material of construction of the apparatus is, essentially, of a corrosion resistant material, such as, stainless steel or glass-lined steel. While the end closures 3 and 4 may be permanently fixed to the cylindrical tube 2, it is preferred that closures 3 and 4 be removable for cleaning and inspection of the inner chamber 5. Nozzle 8 is conveniently adapted for easy replacement e.g. having a threaded barrel for insertion in a corresponding tapped bore in the end closure 4 and having an opposite end portion adapted to receive a driving tool e.g. hexagonal flats arranged to receive a spanner or socket.

The method of preparation of mononitrobenzene utilizing the process of the invention will now be described with reference to FIG. 2. A reaction stream of mixed acid from acid feed vessel 20 is pumped by means of metering pump 21 through acid preheater 22 and into reaction chamber 5 through spray nozzle 8.

Simultaneously, a stream of benzene from benzene feed vessel 23 is pumped by means of metering pump 24 into reaction chamber 5 through orifice 10. The rate of flow of each of the benzene and mixed acid components is controlled by adjusting the operating rates of metering pumps 21 and 24 so that the reactants are delivered into the reaction chamber in slight (1-10%) stoichiometric access of benzene and the reaction temperature is maintained below 145° C. Within reaction chamber 5, the fine particles or spray of mixed acid reacts with the benzene to produce a mixture of substantially homogeneous mononitrobenzene and spent acid which mixture is continuously removed from reaction chamber 5 via line 25 to continuous separator 26. As disclosed by Alexanderson et al in U.S. Pat. No. 4,091,042, advantages can be gained by maintaining conditions such that the nitric acid concentration of the mixed acid is between 3-8.5% and the water concentration is not less than about 25%. The spent acid concentration should provide a sulphuric acid content of from 62-68% to maintain reaction rates and avoid denitration. It may, in some instances, be desirable to subject the nitrobenzene/spent acid mixture exiting through line 25 to a further refining step prior to delivery to separator 26 in order to fully nitrate any residual, unreacted benzene which may remain in the product. Such a refining step may take the form (not shown) of, for example, a static mixer or the use of an orifice plate, installed between the exit of chamber 5 and separator 26. Alternatively, a second reaction chamber similar to chamber 5 may be employed in which the product from line 25 is subjected to further nitration. At separator 26, the spent acid and crude nitrobenzene are separately recovered. The crude nitrobenzene is directed to a washing and purification step (not shown) and the hot spent acid is directed to a concentrator (not shown) where it is restored to its initial concentration by the removal of water by means of external heat. The external heat requirement is reduced since no cooling was applied at the reaction chamber.

EXAMPLE

In a pilot plant trial, an apparatus was prepared consisting of a vertical stainless steel tubular reaction chamber 43 cm in length and 7.5 cm in diameter. An atomixing orifice, 0.5 mm in diameter and 1.2 mm long, for the introduction of benzene, was located centrally in a base plate. An inlet for the introduction of mixed acid was located in the side wall of the tubular chamber about 15 cm above the base plate and orifice. Mixed acid at about 100° C. comprising a mixture of 5.08% by weight of nitric acid and 61.89% by weight of sulphuric acid was delivered into the chamber at a rate of 573.2 ml/min. When steady acid flow was achieved, benzene at ambient temperature was injected through the atomizing orifice into the mixed acid at a rate of 75.2 ml/min. The reaction was continued for 30 minutes during which time samples were taken for analysis. From the analysis, the rate of convention, based on nitric acid, was 55.3% and on the organic phase, was 52.5%. Optimization of these conditons in a full-scale plant can be expected to produce close to 100% conversion.

While the invention herein disclosed has been described in terms of the particular process for the nitration of benzene in the production of nitrobenzene, it will be appreciated and understood by those skilled in the art that other nitratable organic compounds may be reacted with mixed acid employing the disclosed process. Amongst the nitratable organic compounds, in addition to benzene, which may be reacted employing process are, for example, toluene, dimethylbenzene, halobenzene, naphthalene, methylnaphthalene, halonaphthalene, halotoluene and halomethylnaphthalene.

I claim:

1. A continuous process of producing a mononitrated organic compound by the reaction of a liquid sulphuric acid/nitric acid mixture with a liquid nitratable organic compound in an amount sufficient to fully utilize the nitric acid content of said acid mixture, comprising the step of forming a turbulent jet of said mixed acid to produce droplets of mixed acid having a size of from less than 1 μm to about 10 μm diameter and contacting the said acid droplets with the said nitratable organic compound in an amount sufficient to produce a mononitrated organic compound.

2. A continuous process of producing a mononitrated organic compound by the reaction of a liquid sulphuric acid/nitric acid mixture with a liquid nitratable organic compound in an amount to fully utilize the nitric acid content of the said acid mixture, comprising the step of forming a turbulent jet of said organic compound to produce droplets thereof of a size of from less than 1 μm to about 10 μm diameter and contacting the said droplets of organic compound with the said acid mixture in an amount sufficient to produce a mononitrated organic compound.

3. A process as claimed in any one of claims 1 or 2 wherein the nitratable organic compound is selected from the group consisting of benzene, toluene, dimethylbenzene, halobenzene, napthalene, methylnaphthalene, halonaphthalene, halotoluene and halomethylnaphthalene.

4. A process as claimed in any one of claims 1 or 2 wherein the said mixed acid comprises from 3 to 8.5% by weight of nitric acid, from 58.5 to 70.0% by weight of sulphuric acid and not less than about 25% by weight of water.

* * * * *